United States Patent [19]

Reetz et al.

[11] 4,429,145
[45] Jan. 31, 1984

[54] PREPARATION OF TRIMETHYLSILYL CYANIDE

[75] Inventors: Manfred T. Reetz, Marburg; Ioannis Chatziiosifidis, Buehlertal, both of Fed. Rep. of Germany

[73] Assignee: Bayer Aktiengesellschaft, Leverkusen, Fed. Rep. of Germany

[21] Appl. No.: 417,961

[22] Filed: Sep. 14, 1982

[30] Foreign Application Priority Data

Oct. 3, 1981 [DE] Fed. Rep. of Germany ....... 3139456

[51] Int. Cl.³ .............................................. C07F 7/10
[52] U.S. Cl. .................................................. 556/415
[58] Field of Search ....................................... 556/415

[56] References Cited

U.S. PATENT DOCUMENTS 3,032,575  5/1962  Freitag et al. ...................... 556/415
3,330,628  7/1967  Johns ............................... 556/415 X
4,328,351  5/1982  Findeisen et al. .

FOREIGN PATENT DOCUMENTS 40356  5/1981  European Pat. Off. ............ 556/415
53-132525  11/1978  Japan .................................. 556/415

OTHER PUBLICATIONS

Synthesis, 1979, pp. 522–524.

Primary Examiner—Paul F. Shaver

[57] ABSTRACT

Trimethylsilyl cyanide, $(CH_3)_3Si$-CN, is obtained by reacting trimethylsilyl chloride with an approximately equimolar amount of an alkali metal cyanide in the absence of water and in the presence of catalytic, substoichiometric amounts of both an alkali metal iodide and N-methylpyrrolidone, at a temperature of from 15°–25° C.

8 Claims, No Drawings

PREPARATION OF TRIMETHYLSILYL CYANIDE

The invention relates to an unobvious process for the preparation of trimethylsilyl cyanide from trimethylsilyl chloride. Trimethylsilyl cyanide is a valuable, versatile intermediate product in organic syntheses.

The best methods known at present for the preparation of trimethylsilyl cyanide originate from S. Hünig et al. (Synthesis 1979, page 522) and J. K. Rasmussen et al. (Synthesis 1979, page 523), and both methods use trimethylsilyl chloride and an alkali metal cyanide as starting materials. According to Hünig, trimethylsilyl chloride is reacted with excess sodium cyanide (22% excess) in the presence of a phase-transfer catalyst and in the presence of N-methylpyrrolidone as the solvent, for 30-36 hours at 90°-100° C., 60-70% of isolated trimethylsilyl cyanide being obtained. According to Rasmussen, the trimethylsilyl chloride is reacted with excess potassium cyanide (250% excess) in N-methylpyrrolidone for 16 hours at reflux temperatures, and 71% of trimethylsilyl cyanide, isolated by distillation, is obtained.

Apart from the moderate yields, both process variants are associated with the disadvantages that the alkali metal cyanide must be employed in excess, and that relatively long reaction times and relatively high temperatures are required. In addition, a phase-transfer catalyst must be added in one of the two process variants, as indicated.

The present invention now provides a process for the preparation of trimethylsilyl cyanide, $(CH_3)_3Si\text{-}CN$, by reacting trimethylsilyl chloride with an alkali metal cyanide in the presence of N-methyl-pyrrolidone, in which the trimethylsilyl chloride is reacted with an approximately equimolar amount of an alkali metal cyanide in the absence of water and in the presence of catalytic, sub-stoichiometric amounts of both an alkali metal iodide and N-methylpyrrolidone, at room temperature (15°-25° C.).

Surprisingly, the trimethylsilyl chloride can thereby be obtained in high yield and purity, the reaction time for complete conversion being typically about 12 hours.

The process according to the invention avoids the disadvantages of previously known methods, and thus represents a substantial improvement. Thus, the alkali metal cyanide need be employed only in stoichiometric amounts, and no longer in excess. The N-methylpyrrolidone, as well as the catalytically active alkali metal iodide, need be employed only in a sub-stoichiometric amount, and not as a solvent. At the same time, substantially higher yields (up to 90% of theory) are achieved under milder reaction conditions, at a temperature which is not elevated and in reaction times which nevertheless are greatly reduced.

If trimethylsilyl chloride is reacted, by the process according to the invention, with potassium cyanide in the presence of (a catalytic amount of) potassium iodide, the course of the reaction can be represented by the following equation

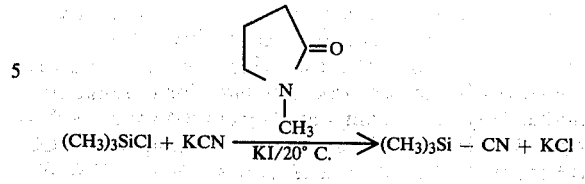

Sodium cyanide or potassium cyanide is preferably used as the alkali metal cyanide. Potassium iodide or sodium iodide is preferably used as the alkali metal iodide.

In carrying out the process according to the invention, trimethylsilyl chloride and the alkali metal cyanide are preferably reacted in exactly stoichiometric amounts. In contrast, the alkali metal iodide and N-methylpyrrolidone are employed in sub-stoichiometric amounts, the alkali metal iodide in general in amounts of 5-15 mol %, preferably of 8-12 mol %, and the N-methylpyrrolidone in general in amounts of 15-25 mol %, preferably of 18-23 mol %, in each case relative to the amount of trimethylsilyl chloride or alkali metal cyanide used.

Complete conversion can also be achieved without the addition of N-methylpyrrolidone, but this requires considerably longer reaction times (65 hours at 22° C.) and the use of a mechanical stirrer.

The reaction is carried out in general under normal pressure. An inert gas atmosphere is not required, but the reaction must be carried out in the absence of moisture. The reaction is therefore carried out in a reaction vessel which is thoroughly dried and protected from atmospheric humidity, using carefully dried reagents, if required. It is particularly advantageous initially to introduce a suspension of the alkali metal cyanide and the alkali metal iodide in trimethylsilyl chloride, then to add the N-methylpyrrolidone, and then to stir the reaction mixture at room temperature until complete conversion has occurred (approximately 12 hours).

The trimethylsilyl cyanide is obtained in pure form most simply by direct distillation from the reaction vessel. The yields are 87-90% of theory.

Trimethylsilyl cyanide is a valuable, versatile intermediate product of organic chemistry; it is used, for example, for converting aldehydes and ketones into silylated cyanohydrins, which in turn are known to be useful, reactive intermediate products (see Synthesis 1980, page 861; and also Synthesis 1979, pages 522 and 523). Trimethylsilyl cyanide can be used, in particular, as a starting material for the preparation of acyl cyanides (see, for example, Synthesis 1979, pages 204 to 205), which in turn can be employed for the synthesis of 1,2,4-triazin-5-ones, which possess outstanding herbicidal properties.

Thus, trimethylsily cyanide can readily be converted into pivaloyl cyanide, for example by reaction with pivaloyl chloride, thus

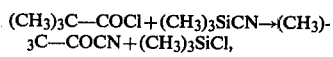

and pivaloyl cyanide can be converted by known processes into, for example, the herbicidally active compound 3-methylthio-4-amino-6-tert.-butyl-1,2,4-triazin-5(4H)-one (see, for example, German Patent Specification No. 1,795,784, DE-OS (German Published Specification) No. 2,733,180, U.S. Pat. No. 4,175,188, and also DE-OS (German Published Specifications) Nos. 3,003,203, 3,003,541 and 3,009,043).

By reaction with benzoyl chloride, trimethylsilyl cyanide can be converted analogously into benzoyl cyanide (see Example 3 infra), which can also be further converted by known processes into, for example, the herbicidally active compound 3-methyl-4-amino-6-phenyl-1,2,4-triazin-5(4H)-one (see, for example, DE-OS (German Published Specifications) Nos. 2,224,161, 2,364,474, 2,528,211 and 2,708,189).

The examples which follow are intended to illustrate the invention further.

EXAMPLE 1

65.1 g (1 mol) of dry potassium cyanide were initially introduced into a 250 ml round-bottomed flask, the flask was closed with a drying tube (filled with calcium chloride) and was heated with a Bunsen burner for a short time. (However, it could also be dried beforehand in a drying pistol.) After the flask had been cooled, 16.5 g (0.1 mol) of potassium iodide and 108.2 g (1 mol) of trimethylsilyl chloride were introduced. 19.8 g (0.2 mol) of N-methylpyrrolidone were added to this suspension, and the reaction mixture was then stirred at 22° C. for 12 hours (by means of a magnetic stirrer). An H-NMR spectrum of the reaction mixture then showed complete conversion. The trimethylsilyl cyanide formed was isolated by direct distillation from the reaction vessel, at a boiling point of 112°-117° C.; 87.2 g (about 88% of theory) of pure trimethylsilyl cyanide were obtained.

EXAMPLE 2

The reaction of sodium cyanide (1 mol) and trimethylsilyl chloride (1 mol) in the presence of sodium iodide (0.1 mol) and N-methylpyrrolidone (0.2 mol) proceeded completely analogously, yields of trimethylsilyl cyanide of 87°-90% of theory being obtained. In this case, the sodium iodide could also be replaced by potassium iodide (0.1 mol). The working-up was effected by distillation, as in Example 1.

The H-NMR spectrum of the distilled product (singlet at $\delta = 0.1$ ppm in $CCl_4$) did not indicate the presence of any impurities. The product was hygroscopic, and therefore had to be protected from atmospheric humidity. It solidified in a refrigerator (melting point approximately 15° C.).

EXAMPLE 3

The reaction of trimethylsilyl cyanide to give benzoyl cyanide

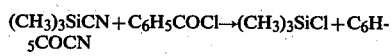

was carried out as follows.

70.3 g (0.5 mol) of benzoyl chloride were initially introduced into a 250 ml four-necked flask (provided with a stirrer, thermometer, dropping funnel and mounted distillation bridge), and were warmed to 110° C. 49.5 g (0.5 mol) of trimethylsilyl cyanide were added dropwise in the course of 20 minutes; the trimethylsilyl chloride formed in this reaction was distilled off simultaneously. The residue was fractionally distilled in vacuo.

Yield: 53 g (82% of theory) of benzoyl cyanide of boiling point 86° to 88° C./11 mbar and melting point 31° C.

It will be appreciated that the instant specification and examples are set forth by way of illustration and not limitation, and that various modifications and changes may be made without departing from the spirit and scope of the present invention.

We claim:

1. In the preparation of trimethylsilyl cyanide, $(CH_3)_3Si\text{-}CN$, by reacting trimethylsilyl chloride and and alkali metal cyanide in the presence of N-methylpyrrolidone, the improvement which comprises effecting the reaction with an approximately equimolar amount of alkali metal cyanide and trimethylsilyl chloride in the substantial absence of water and in the presence of catalytic, sub-stoichiometric amounts of both an alkali metal iodide and N-methylpyrrolidone, at a temperature of about 15° to 25° C.

2. A process according to claim 1, wherein the alkali metal iodide is employed in about 5-15 mol % relative to the amount of trimethylsilyl chloride or alkali metal cyanide used.

3. A process according to claim 1, wherein the alkali metal iodide is employed in about 8-12 mol % relative to the amount of trimethylsilyl chloride or alkali metal cyanide used.

4. A process according to claim 1, wherein the N-methylpyrrolidone is employed in about 15-25 mol % relative to the amount of trimethylsilyl chloride or alkali metal cyanide used.

5. A process according to claim 1, wherein the N-methylpyrrolidone is employed in about 18-23 mol % relative to the amount of trimethylsilyl chloride or alkali metal cyanide used.

6. A process according to claim 1, wherein sodium cyanide or potassium cyanide is employed as the alkali metal cyanide.

7. A process according to claim 1, wherein potassium iodide or sodium iodide is used as the alkali metal iodide.

8. A process according to claim 3, wherein the N-methylpyrrolidone is employed in about 18-23 mol % relative to the amount of trimethylsilyl chloride or alkali metal cyanide used, sodium cyanide or potassium cyanide is employed as the alkali metal cyanide, and potassium iodide or sodium iodide is used as the alkali metal iodide.

* * * * *